United States Patent
Nicolas

(10) Patent No.: US 9,061,052 B2
(45) Date of Patent: Jun. 23, 2015

(54) AQUEOUS EXTRACT OF TOBACCO LEAVES, ITS USES IN THE TREATMENT OF DEPENDENCE

(75) Inventor: Jean-Pierre Nicolas, Ste Cecile les Vignes (FR)

(73) Assignee: NFL BIOSCIENCE, Paris (FR)

( * ) Notice: Subject to any disclaimer, the term of this patent is extended or adjusted under 35 U.S.C. 154(b) by 897 days.

(21) Appl. No.: 12/299,850

(22) PCT Filed: May 9, 2007

(86) PCT No.: PCT/FR2007/000786
§ 371 (c)(1),
(2), (4) Date: Nov. 6, 2008

(87) PCT Pub. No.: WO2007/128924
PCT Pub. Date: Nov. 15, 2007

(65) Prior Publication Data
US 2009/0142426 A1   Jun. 4, 2009

(30) Foreign Application Priority Data
May 9, 2006 (FR) .................................. 06 04104

(51) Int. Cl.
*A61K 33/02* (2006.01)
*A61K 36/81* (2006.01)

(52) U.S. Cl.
CPC ...................................... *A61K 36/81* (2013.01)

(58) Field of Classification Search
CPC .............................. A01N 65/38; A61K 36/82
See application file for complete search history.

(56) References Cited

U.S. PATENT DOCUMENTS

2003/0185908 A1   10/2003   Williams et al.

FOREIGN PATENT DOCUMENTS

| EP | 0 796 621 | 9/1997 |
|---|---|---|
| EP | 1 304 048 | 4/2003 |
| IE | 960 511 | 1/1998 |
| JP | S64-68326 | 3/1989 |
| JP | H9-249575 | 9/1997 |

OTHER PUBLICATIONS

Jensen et al. "Fermentation of Cigar-Type Tobacco". Industrial and Engineering Chemistry, vol. 42, No. 3 (Mar. 1950) pp. 519-522.*
Jones et al. "Subjective and Physiological Effects of Intravenous Nicotine and Cocaine in Cigarette Smoking Cocaine Abuse". The Journal of Pharmacology and Experimental Therapeutics (1999) 188-197.*
Wickes Felter et al. "Tabacum (U.S.P.-Tobacco" from King's American Dispensatory (1898) [retrieved on Mar. 11, 2011]. Retrieved from the Internet : <URL: http://www.henriettesherbal.com/eclectic/kings/nicotiana.html>.*
Houezec et al. "A clinical pharmacological study of subcutaneous nicotine". European Journal of Clinical Pharmacology, vol. 44 (1993) 225-230.*
Henningfield, J. E. "Nicotine Medications for Smoking Cessation" in The New England Journal of Medicine, Edited by Alastair J.J. Wood, M.D., vol. 333, No. 18 (1995) 1196-1203.*
Anthenelli, R.M., "Recent advances in the treatment of tobacco dependence," Clinical Neuroscience Research, vol. 5 (2005) pp. 175-183.
International Search Report dated Feb. 22, 2008 for Application No. PCT/FR2007/000786.
English Translation of Japanese Office Action dated Sep. 4, 2012 for Application No. 2009-508426.
English Abstract of Japanese Application No. JP S64-68326, Mar. 14, 1989.
English Abstract of Japanese Application No. JP H9-249575, Sep. 22, 1997.

* cited by examiner

*Primary Examiner* — Amy L Clark
(74) *Attorney, Agent, or Firm* — McAndrews, Held & Malloy Ltd.

(57) ABSTRACT

The invention relates to the use of an aqueous extract of tobacco leaves for the preparation of a medicament for the treatment of dependence, in particular tobacco dependence, and to a sterile injection solution and a kit which can be used for the treatment of dependence, in particular of tobacco.

8 Claims, No Drawings

AQUEOUS EXTRACT OF TOBACCO LEAVES, ITS USES IN THE TREATMENT OF DEPENDENCE

A subject of the present invention is the use of an extract of tobacco leaves for the preparation of a medicament intended for the treatment of dependence. A subject of the invention is also a solution and an injection kit comprising extracts of tobacco leaves.

Dependence or addiction has been defined by the World Health Organization as "a syndrome for which the consumption of a product becomes a requirement greater than those of other behaviours which were previously more important. In its extreme form the state of dependence is characterized by an irresistible need for a product which compels the individual suffering from this dependence to impulsively seek this product".

In France there are thought to be approximately 200,000 individuals dependent on heroin and a much smaller number dependent on cocaine or amphetamine derivatives. However, other products, the effects of which attract less attention, lead to dependence: alcohol, tobacco, coffee. This dependence also leads to significant public health problems.

Thus, there are at present three major types of dependence treatment, in particular against tobacco dependence, apart from behavioural psychotherapy or acupuncture:
nicotine substitutes;
Zyban®;
homeopathy.

The principle of action of these methods is based on the assumption that nicotine is involved in the tobacco dependency mechanism. This molecule can bind to proteins present at the surface of the nerve cells, the nicotinic acetylcholine receptors. In the presence of nicotine, these receptors, which are in fact channels, open. A cascade of events then follows, resulting in the release of a hormone, dopamine. The nicotine stimulates the "reward circuit" and thus produces a sensation of satisfaction.

When people stop smoking, their body "craves" its dose of nicotine in order to satisfy this sensation of wellbeing: this is withdrawal.

The purpose of the nicotine substitutes is therefore to provide the smoker's brain with a quantity of nicotine sufficient to prevent withdrawal symptoms.

The nicotine substitutes can be administered in various ways, by the transdermal route in the form of patches or plasters, by oral route in the form of chewing gums, tablets to suck or sublingual tablets, or via the airways in the form of an inhaler. The oral forms can be used alone or in combination with a patch, as required. The patches or plasters deliver nicotine which is easily absorbed by the skin making it possible to alleviate the physical withdrawal symptoms associated with the absence of nicotine.

The use of patches is recommended by the experts of the Ministry of Health. Although motivation is the essential factor for success, it is thought that the effectiveness of breaking nicotine addiction is doubled compared with a placebo after the use of patches. In total, approximately 16 to 20% of smokers stop smoking after one year as a result of this aid.

Nicotine chewing gums allow nicotine to be delivered in buccal form, which relieves physical withdrawal symptoms. The number of pieces of gum to be chewed can be adjusted according the level of pharmacological dependence which is assessed, as the patches, by responses to the Fagerström test. The consumption of chewing gums generally continues for three months and it is recommended that they should not be used for more than six months after ceasing to smoke.

Several therapeutic tests have demonstrated that the effectiveness of these gums is comparable to that of patches, with a cessation rate of 19% at one year.

In order to obtain an optimum effect, the dose and the duration of treatment must be sufficient and the method of use must be followed (sucking at first and then chewing very slowly for 30 to 40 minutes). In fact, if the chewing is too quick, the nicotine diffuses too quickly and there is a risk of hypersalivation and sometimes dyspepsia or hiccups. Moreover, gum is partially ineffective when swallowed, as it is destroyed to a large extent in the liver. In addition, some ex-smokers seem to experience difficulties in doing without the gums.

Gums can be used to complement plasters to calm a sudden urge to smoke which is not prevented by the latter. They are very suitable in the case of persons who used to smoke irregularly and they allow ex-smokers to play an active role in cessation. They also allow a certain gestural pattern to be maintained.

Nicotine can also be provided in the form of tablets to be placed under the tongue or to suck.

Use of these tablets is more discreet and easier than chewing gums.

As with the other nicotine substitutes, these tablets can cause headaches at the start of treatment.

Nicotine can also be provided by inhalation. The inhaler comprises a mouthpiece with a cartridge resembling a cigarette holder and delivers nicotine in the form of buccal inhalations. On experiencing an urge to smoke, the ex-smoker inhales a mouthful which supplies approximately 5 mg of nicotine.

The inhaler makes it possible not only to alleviate the withdrawal symptoms associated with the absence of nicotine, but also to act on the gestural pattern by mimicking the act of smoking. As with chewing gums and tablets for sucking or placing under the tongue, it can be used to complement a plaster.

Nicotine blood concentrations are obtained more slowly than when smoking a cigarette, and the smoker must therefore wait for the urge to smoke to pass.

Another method of cessation consists of the administration of bupropion, marketed under the trade mark Zyban® by GlaxoSmithKline which acts on certain cerebral neuromediators such as catecholamines, noradrenaline and dopamine. ZYBAN® is a selective catecholamine neuronal reuptake inhibitor, which gives it anti-depressant properties. This drug, which has also been marketed in the USA since 1989 for its anti-depressant properties, makes it possible to reduce certain symptoms associated with withdrawal such as the urge to smoke and difficulties in concentration.

The effectiveness of Zyban® is equivalent to that obtained after use of nicotine plasters (cessation rate of around 20%). Zyban® has also demonstrated an effective activity in chronic bronchitics in clinical studies, these patients often being heavy smokers who generally have difficulty in giving up tobacco.

Zyban® acts on the psychological component of tobacco dependence and makes it easier to break the nicotine addiction by a mechanism which is different from that of nicotine substitutes.

Zyban® requires a medical prescription and can cause a dry mouth sensation, insomnia and dizziness. This drug has been the subject of drug monitoring measures by the Agence française de sécurité sanitaire des produits de santé (Afssaps) as deaths have been noted in Great Britain after its administration. However, serious reactions to this drug seem to be rare when Zyban® has been correctly prescribed and its contraindications respected.

The third cessation route is homeopathy, which relies on the use of infinitesimal doses, obtained by means of successive dilutions, of the substance provoking the symptoms that it is desired to combat. Thus an extract of "tabacum" is often used in breaking nicotine addiction. Irish Patent Application IE 960 511 describes in particular the use of homeopathic dilutions of tobacco extract for manufacturing a medication intended to restore neuronal functions.

Its effects have not been demonstrated in breaking nicotine addiction. As with the other unconventional cessation techniques, its effectiveness is not sufficient in the case of heavy smokers.

For the experts of the health ministry, the use of extracts of "tabacum", i.e. aqueous extracts of tobacco leaves, at very low doses (less than 0.00001 g/ml.) is justified only in the treatment of tobacco allergies, which are entirely exceptional. The extract is then administered by mesotherapy treatment according to a very strict protocol.

The dependence or addiction mechanisms are complex and to date have not been fully elucidated. Nevertheless, recent studies have demonstrated that dependence involves the participation of three neuromodulators, dopamine, noradrenaline and serotonin (Jean-Paul Tassin and Jacques Glowinski in Comptes rendus de l'Academie des sciences americaines, 24 Apr. 2006). Malfunction of the kinetics of production of these neuromodulators reflects the presence of the dependence.

Conventionally, nicotine has been regarded as the sole component of the cigarette causing dependence and on this basis, methods of breaking nicotine addiction essentially rely on taking nicotine. This approach is now called into question, since according to the recent studies cited above, nicotine does not appear to be an essential factor in dependence.

Surprisingly and unexpectedly, the present inventor has found that the injection of an aqueous solution of an aqueous extract of tobacco leaves makes it possible to reduce dependence. More particularly, the inventors have been able to demonstrate that a single injection of a tobacco extract according to the invention was generally sufficient to reduce or even eliminate smokers' tobacco dependence. This feature constitutes a major advantage for the patient, given that the products currently available on the market only provide treatments which are long-term and in several doses. Conversely, the treatment according to the invention proposes a shock therapy, i.e. a treatment constituted preferably of a single injection of a tobacco extract, optionally followed after several days or even weeks by at least one second injection if the treated patient feels the need.

The subject of the invention is therefore the use of an aqueous extract of tobacco leaves for the preparation of a medication for the treatment of dependence.

More particularly, the subject of the invention is the use of an aqueous extract of tobacco leaves for the preparation of a medication in the form of a solution in sterile water for injection, preferably for an administration by subcutaneous route, for the treatment of dependence.

The aqueous extract of tobacco leaves comprises numerous compounds, but contains only very small quantities of nicotine and can even be substantially nicotine-free.

Without wishing to be bound by theory, the inventor is of the opinion that the substances present in the aqueous extracts of tobacco leaves act against the pathological decoupling of the three principal neuromodulators, namely dopamine, noradrenaline and serotonin.

According to an advantageous embodiment, the present invention relates to the use of an aqueous extract of tobacco leaves for the preparation of a medicament for the treatment of tobacco dependence.

Advantageously, lyophilizates of aqueous extracts of tobacco leaves are used. In fact, the use of aqueous extracts of tobacco leaves makes it possible to have aqueous extracts of tobacco leaves available at any time of year, without their availability being linked to the tobacco harvest season.

According to an advantageous embodiment, the medicament is presented in the form of a single-dose injection, preferably by subcutaneous route.

The administration of extracts of tobacco leaves results in a lasting (3 to 5 weeks) marked, even complete, reduction in the level of bodily cravings, thus eliminating the urge to take the toxic substance on which the patient is dependent, in particular cigarettes, and the associated stresses. Thus a single injection is generally sufficient to reduce, even eliminate the symptoms of tobacco dependence. Clearly, at least one subsequent additional injection may be necessary depending on the patient treated, in particular depending on his level of tobacco dependence. A person skilled in the art will be able to adjust the time interval between the first and second injection according to each patient, and optionally the number of additional injections.

Without wishing to be bound by theory, the inventor is of the opinion that this method of administration allows the active substances present in the extract of tobacco leaves to enter the bloodstream very rapidly and allow the massive release of the neuromodulators involved in the dependency mechanisms. It is therefore possible to speak of a threshold-effect mechanism obtained by persistent saturation and neutralization of the inductor sites of the stress-circuits. Of course, any administration route which would allow a threshold effect of the same order would be appropriate. Thus, administration by intramuscular route or by intravenous route could be envisaged.

Detoxification is ipso facto possible and initiated. It will take place throughout the whole of the persistence period resulting from the treatment.

The treatment is well tolerated, without the risk of development of any addiction.

According to a particular embodiment, a subject of the invention is the use of an aqueous extract of tobacco leaves having a dry matter content, expressed in mg/ml, of 0.05 to 150 mg of dry matter per ml of sterile water, preferably 0.5 to 100 mg per ml sterile water, and even more preferably 1 to 20 mg per ml sterile water, for the preparation of an injection solution for the treatment of dependence.

Even at high concentrations, the aqueous extracts of tobacco leaves do not appear to be toxic, in particular when they are administered by subcutaneous route. However, the effectiveness of the treatment was not improved by using a content greater than 150 mg/ml. On the other hand, with a content of less than 0.05 mg/ml, the results in terms of effectiveness of the treatment were poorer.

According to the degree of dependence of the patient and his ability to control the associated stress, a single injection can prove to be sufficient.

Thus the subject of the invention is the use of an aqueous extract of tobacco leaves for the preparation of a single injection for the treatment of dependence.

In fact, in particular in the case of tobacco dependence, it was demonstrated that a single injection of aqueous extracts of tobacco leaves was sufficient for the patient to no longer have the signs of dependence, i.e. in particular sleep disturbance, irritability, agitation, hyperactive tonicity. From the first injection, the patient experiences the characteristic signs heralding the success of detoxification: deep sleep, fatigability from the first days, progressive and rapid recovery of smell, taste and sensitivity of the throat.

In other cases, a single injection is not sufficient, it is then necessary to carry out at least a second one.

A subject of the invention is therefore also the use of a aqueous extract of tobacco leaves for the preparation of at least two injections carried out at time intervals of 4 to 30, preferably 5 to 15, even more preferably 6 to 13 days.

The need to carry out a second injection, and optionally other additional injections, is determined for each patient according to the results obtained after the first injection and/or after the above injections.

In the case of tobacco dependence, the number of injections should not be greater than 5, preferably not greater than 4, and even more preferably not greater than 2.

Following this injection or these injections, the patient experiences a strong motivation to ensure the complete success of the detoxification himself.

Of course, for optimum effectiveness, these injections must be combined with the recommendations conventionally made on cessation, i.e. that it is strongly advised to systematically avoid alcohol consumption, strong spices and coffee, as it is recognised that the urge to have a cigarette again is often associated with these tastes and drives a so-called Pavlovian reflex.

The invention also relates to sterile aqueous solutions of aqueous extracts of tobacco leaves having a dried matter content of 0.05 to 150 mg/ml, preferably 0.5 to 100 mg/ml, and even more preferably 1 to 20 mg/ml of sterile water.

Advantageously, the aqueous extracts are lyophilized.

In a particular embodiment, the invention also relates to sterile aqueous solutions of an aqueous extract of tobacco leaves having a dry matter content of 0.05 to 50 mg/ml of sterile water, preferably of 0.5 to 20 mg/ml sterile water, and even more preferably 1 to 15 mg/ml sterile water, said extract preferably being lyophilized.

The invention also relates to a ready-to-use kit comprising a syringe, a flask of sterile water and a lyophilizate of aqueous extract of tobacco leaves.

These aqueous solutions and this kit are intended to be used in the treatment of dependence, more particularly tobacco dependence.

The invention will be described in more detail with reference to the following examples which are given by way of illustration only and are not limitative.

EXAMPLES

Example 1

Preparation of Solutions for Injection

Solutions for injection were prepared by dissolving 20 mg of an IP 100 lyophilizate of tobacco leaves marketed by Société Stallergènes in 2 ml sterile water.

Example 2

150 patients suffering from tobacco dependence responded to a questionnaire on allergies, cardio-vascular risk, diabetes, alcohol sensitivity, chemical toxins or known drugs.

Each of the 150 patients then received a subcutaneous injection (in the forearm or buttocks) of a solution prepared as above.

10 to 12 days later, 15 patients who still felt the urge to smoke received a second injection identical to the first.

The percentage of patients not having taken up cigarettes again at the end of 1 month, 3 months, 6 months and 12 months is given below as the success rate:

Success Rate:
1 MONTH: 74% of which 69% had one injection and 5% had two injections.
3 MONTHS: 61%
6 MONTHS: 57%
12 MONTHS: 53%

The percentage of patients having started smoking again 1 month after the last injection is given below as the failure rate:

Failure Rate:
1 MONTH: 26% of which 25% had one injection and 1% had two injections.

The failure rate of 26% should theoretically be reduced to 10% by systematically performing the second injection. The results at 3, 6, and 12 months would thus be improved accordingly.

The results obtained are therefore markedly superior to the products currently on the market:
16 to 20% success for the plasters, patches or gums after one year's treatment,
20% success for Zyban®.

The treatment is of short duration and much less expensive than the current treatments over several months.

The invention claimed is:

1. A method for treating tobacco dependence in a subject in need thereof, wherein said method comprises subcutaneously injecting into the patient in need thereof a solution containing an effective amount of an aqueous extract of tobacco leaves and sterile water, wherein said aqueous extract of tobacco leaves has a dried matter content of 0.05 to 150 mg/ml, and wherein said aqueous extract of tobacco leaves is substantially nicotine-free.

2. The method of claim 1, wherein said aqueous extract is lyophilized.

3. The method of claim 1, wherein said aqueous extract has a dry matter content of 0.5 to 100 mg of dry extract of tobacco leaves per ml of sterile water.

4. The method of claim 1, wherein said aqueous extract has a dry matter content of 1 to 20 mg of dry extract of tobacco leaves per ml of sterile water.

5. The method of claim 1, wherein said method comprises a single injection of the solution to the patient.

6. The method of claim 1, wherein said method comprises at least two injections of the solution to the patient, wherein said at least to injections are performed at time intervals of 4 to 30 days.

7. The method of claim 6, wherein the at least two injections are performed at time intervals of 5 to 15 days.

8. The method of claim 6, wherein the at least two injections are performed at time intervals of 6 to 13 days.

* * * * *